United States Patent
Lagodzki

(10) Patent No.: US 9,005,197 B2
(45) Date of Patent: Apr. 14, 2015

(54) MEDICAL INSTRUMENT FOR ABLATING TISSUE

(75) Inventor: Karol Lagodzki, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 778 days.

(21) Appl. No.: 13/279,924

(22) Filed: Oct. 24, 2011

(65) Prior Publication Data

US 2012/0101499 A1    Apr. 26, 2012

Related U.S. Application Data

(60) Provisional application No. 61/406,753, filed on Oct. 26, 2010.

(51) Int. Cl.
*A61B 18/14* (2006.01)
*A61B 18/00* (2006.01)

(52) U.S. Cl.
CPC ....... *A61B 18/14* (2013.01); *A61B 2018/00577* (2013.01); *A61B 2018/1407* (2013.01); *A61B 2018/1425* (2013.01)

(58) Field of Classification Search
CPC ..... A61B 18/1492; A61B 18/14; A61B 18/12
USPC ................... 606/41, 32, 50, 18, 48
See application file for complete search history.

(56) References Cited

U.S. PATENT DOCUMENTS

| | | |
|---|---|---|
| 5,830,210 A | 11/1998 | Rudko et al. |
| 6,014,590 A | 1/2000 | Whayne et al. |
| 6,071,282 A | 6/2000 | Fleischman |
| 6,163,716 A | 12/2000 | Edwards et al. |
| 6,640,120 B1 | 10/2003 | Swanson et al. |
| 7,399,299 B2 | 7/2008 | Daniel et al. |
| 7,615,049 B2 | 11/2009 | West et al. |
| 2005/0251134 A1* | 11/2005 | Woloszko et al. ............ 606/46 |
| 2007/0083194 A1* | 4/2007 | Kunis et al. .................. 606/41 |
| 2009/0093802 A1 | 4/2009 | Kulesa et al. |
| 2009/0240248 A1 | 9/2009 | Deford et al. |
| 2010/0049189 A1 | 2/2010 | Dickens |
| 2010/0179530 A1 | 7/2010 | Long et al. |

FOREIGN PATENT DOCUMENTS

| | | |
|---|---|---|
| EP | 1 319 364 B1 | 3/2007 |
| EP | 2 204 135 A2 | 7/2010 |
| WO | WO 2009/105720 A2 | 8/2009 |

* cited by examiner

*Primary Examiner* — Christopher D Koharski
*Assistant Examiner* — Michael Carey
(74) *Attorney, Agent, or Firm* — Brinks Gilson & Lione

(57) ABSTRACT

A medical instrument is provided for a ablating tissue. The medical instrument has an inner bipolar electrode and an outer bipolar electrode. The inner and outer electrodes are separated by an insulation layer. The inner and outer electrodes form a loop that may be rotated around a tumor to ablate the tumor tissue.

20 Claims, 3 Drawing Sheets

MEDICAL INSTRUMENT FOR ABLATING TISSUE

This application claims the benefit under 35 U.S.C. §119 (e) of U.S. Provisional Application No. 61/406,753, filed Oct. 26, 2010, which is hereby incorporated by reference herein.

BACKGROUND

The present invention relates generally to medical devices and more particularly to an ablation instrument for isolating tissue, such as a tumor.

Various types of ablation techniques have been used to treat tumors in a patient. For example, one type of ablation technique involves using a bipolar electrode connected to a bipolar energy generator. Typically, a bipolar electrode has two poles that are spaced away from each other. Applying a charge to the poles from the bipolar generator causes tissue adjacent the poles to heat up. By adjusting the charge from the bipolar generator, the adjacent tissue can be heated to such a degree that a region of adjacent tissue is burned and killed. One type of bipolar electrode that is used to treat tumors is formed in the shape of a loop. Once the electrode is energized, the looped electrode can then be rotated around the tumor in order to burn and kill the tumor tissue.

However, several problems remain with existing ablation techniques. For example, one problem is that it can be difficult to fully kill the tumor tissue without causing excessive damage to surrounding healthy tissue. This can have several negative consequences. In particular, if the energy is adjusted to minimize damage to surrounding healthy tissue, all of the tumor tissue may not be killed. For example, when the bipolar electrode has a circular shape, tumor tissue located closer to the electrode absorbs more heat, but tumor tissue located farther from the electrode absorbs less heat. In other words, tumor tissue located at the center of the circular electrode may not be heated sufficiently to kill the tumor tissue at the center. This situation can allow the surviving tumor tissue to continue to grow, which eventually can result in recurrence of the tumor or metastasis of the tumor tissue.

On the other hand, adjusting the energy of the bipolar electrode higher to ensure a higher percentage of killed tumor tissue also results in more healthy tissue being killed or damaged. Thus, physicians can be faced with a difficult and complex task of adjusting energy settings of bipolar electrodes to achieve maximum tumor ablation while minimizing damage to surrounding healthy tissue. This challenge can become even more difficult when a tumor is located close to a crucial organ. In this case, the energy settings may need to be set particularly low to avoid causing critical damage to the nearby organ. However, such low energy settings may be ineffective in treating the tumor.

Accordingly, the inventor believes it would be desirable to provide a new medical instrument for ablating tissue that may be used to increase control over the ablation region.

SUMMARY

A medical instrument is described that has two bipolar electrodes. The inner bipolar electrode has first and second poles separated by a space. The outer bipolar electrode has third and fourth poles separated by a space. The inner and outer electrodes may be operated independently of each other to maximize ablation of a tumor while minimizing damage to surrounding healthy tissue.

The invention may include any of the following aspects in various combinations and may also include any other aspect described below in the written description or in the attached drawings.

A medical instrument for ablating tissue, comprising: first and second electrical poles extending around a loop configuration, the first and second poles being spaced apart from each other at least a first distance around the loop configuration, the first and second poles being capable of providing a first electrical charge across the first distance; third and fourth electrical poles extending around the loop configuration, the third and fourth poles being spaced apart from each other at least a second distance around the loop configuration, the third and fourth poles being capable of providing a second electrical charge across the second distance; an insulation layer separating the first and second poles from the third and fourth poles, the first and second poles facing toward an exterior of the loop configuration and the third and fourth poles facing toward an inner region of the loop configuration; wherein the loop configuration is rotatable around a tissue portion to ablate tissue circumferentially around the tissue portion to thereby isolate the tissue portion from adjacent tissue, the first and second electrical charges being independent of each other.

The medical instrument wherein the first distance is narrower than the second distance.

The medical instrument wherein at least one of the third and fourth poles comprises teeth facing toward the other of the first and second poles.

The medical instrument wherein the first and second poles are flat ribbons comprising a thickness and a width wider than the thickness, the width facing toward the exterior and an inner surface of the width being adhered to the insulation layer.

The medical instrument further comprising a non-conductive sharp tip disposed at a distal end of the loop configuration, the sharp tip being attached to the insulation layer and extending outward from between the first and second poles.

The medical instrument wherein an open space extending across the first distance is disposed between the first and second poles.

The medical instrument further comprising a non-conductive cutting blade disposed around a majority of the loop configuration, the cutting blade being attached to the insulation layer and extending outward from between the first and second poles.

The medical instrument further comprising a raised insulation portion disposed around the loop configuration between the third and fourth poles, the raised insulation portion being attached to the insulation layer and extending between and inward beyond inner facing surfaces of the third and fourth poles.

The medical instrument further comprising a non-conductive cutting blade disposed around a majority of the loop configuration, the cutting blade being attached to the insulation layer and extending inward from between the third and fourth poles.

The medical instrument further comprising an insulation portion disposed around the loop configuration between the third and fourth poles, the insulation portion being attached to the insulation layer and extending between and inward at least to inner facing surfaces of the third and fourth poles.

The medical instrument further comprising an insulation portion disposed around the loop configuration between the first and second poles, the insulation portion being attached to the insulation layer and extending between and outward at least to outer facing surfaces of the first and second poles.

The medical instrument wherein the first and second poles and the third and fourth poles are made from self-expanding nitinol with an unstressed state in the loop configuration, the first and second poles and the third and fourth poles being compressible into a collapsed configuration adapted to slide within a catheter.

The medical instrument wherein a distal end of the loop configuration is attached to a first longitudinal member and a proximal end of the loop configuration is attached to a second longitudinal member, the first and second longitudinal members being axially moveable relative to each other to stretch and compress the first and second poles and the third and fourth poles between the loop configuration and a collapsed configuration.

The medical instrument wherein the first distance is narrower than the second distance, the first and second poles are flat ribbons comprising a thickness and a width wider than the thickness, the width facing toward the exterior and an inner surface of the width being adhered to the insulation layer, further comprising a first insulation portion disposed around the loop configuration between the first and second poles, the first insulation portion being attached to the insulation layer and extending between and outward at least to outer facing surfaces of the first and second poles, and further comprising a second insulation portion disposed around the loop configuration between the third and fourth poles, the second insulation portion being attached to the insulation layer and extending between and inward at least to inner facing surfaces of the third and fourth poles.

The medical instrument further comprising a non-conductive sharp tip disposed at a distal end of the loop configuration, the sharp tip being attached to the insulation layer and extending outward from between the first and second poles.

The medical instrument further comprising a non-conductive cutting blade disposed around a majority of the loop configuration, the cutting blade being attached to the insulation layer and extending outward from between the first and second poles, and further comprising a raised insulation portion disposed around the loop configuration between the third and fourth poles, the raised insulation portion being attached to the insulation layer and extending between and inward beyond inner facing surfaces of the third and fourth poles.

The medical instrument wherein the first and second poles and the third and fourth poles are made from self-expanding nitinol with an unstressed state in the loop configuration, the first and second poles and the third and fourth poles being compressible into a collapsed configuration adapted to slide within a catheter.

The medical instrument wherein the first and second poles are flat ribbons comprising a thickness and a width wider than the thickness, the width facing toward the exterior and an inner surface of the width being adhered to the insulation layer, further comprising a non-conductive sharp tip disposed at a distal end of the loop configuration, the sharp tip being attached to the insulation layer and extending outward from between the first and second poles, and further comprising a raised insulation portion disposed around the loop configuration between the third and fourth poles, the raised insulation portion being attached to the insulation layer and extending between and inward beyond inner facing surfaces of the third and fourth poles.

The medical instrument further comprising a non-conductive cutting blade disposed around a majority of the loop configuration, the cutting blade being attached to the insulation layer and extending outward from between the first and second poles, and further comprising an insulation portion disposed around the loop configuration between the first and second poles, the insulation portion being attached to the insulation layer and extending between and outward at least to outer facing surfaces of the first and second poles.

The medical instrument wherein the first distance is narrower than the second distance, and the first and second poles and the third and fourth poles are made from self-expanding nitinol with an unstressed state in the loop configuration, the first and second poles and the third and fourth poles being compressible into a collapsed configuration adapted to slide within a catheter.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
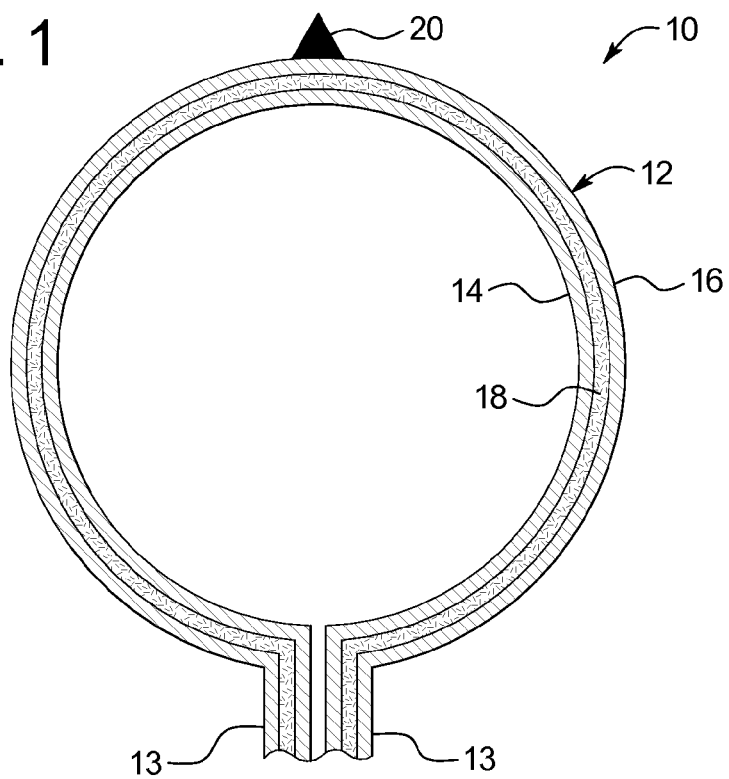
FIG. 1 is a side view of a medical instrument.
Figure 2:
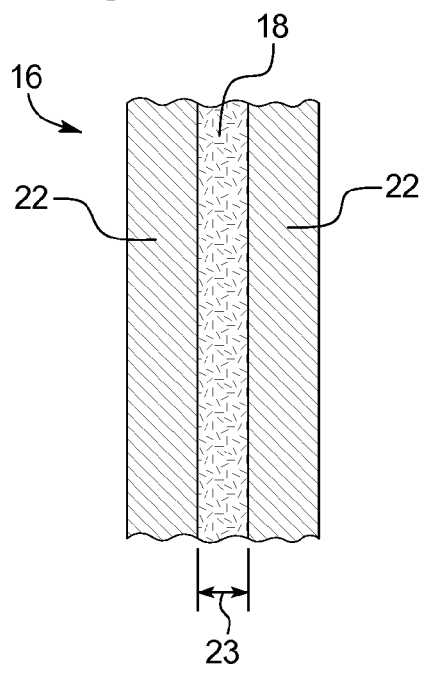
FIG. 2 is a top view of an outer electrode.
Figure 3:
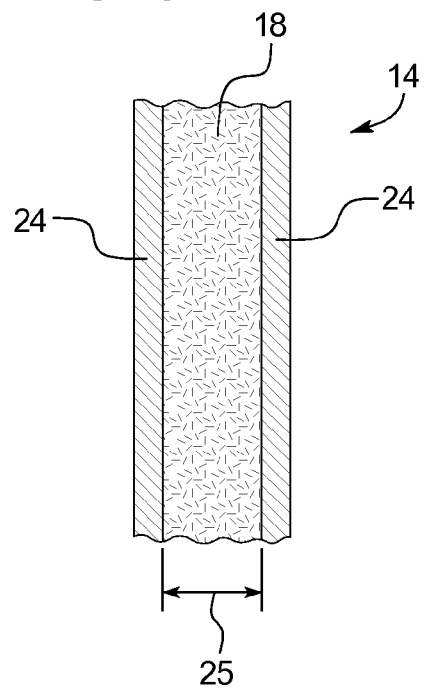
FIG. 3 is a top view of an inner electrode.

Referring now to the figures, and particularly to FIGS. 1-3, a medical instrument 10 is shown, which may be used for ablating tissue, such as tumors. As shown in FIG. 1, the medical instrument 10 may be formed in the shape of a circular loop 12. The medical instrument 10 has two bipolar electrodes 14, 16 that extend around the loop 12. Specifically, one of the electrodes 16 extends around the outside of the loop 12 and faces outward. The other electrode 14 extends around the inside of the loop 12 and faces inward. The two electrodes 14, 16 are separated from each other by an insulation layer 18 that extends around the loop 12 between the two electrodes 14, 16. A sharp tip 20 may be provided at the distal end of the loop 12 for cutting through tissue during delivery of the medical instrument 10 to the treatment site. The ends 13 of the electrodes 14, 16 extend proximally away from the loop 12 and may be connected to wires or other conductors that extend to the proximal end of instrument 10. The proximal end of the conductors are typically connected to electrical connectors that may be connected to a bipolar energy generator.

As shown in FIG. 2, the outer electrode 16 has first and second electrical poles 22. The first and second poles 22 are spaced apart and separated from each other around the loop 12 so that there is no direct electrical contact between the first and second poles 22. As shown in FIG. 3, the inner electrode 14 has third and fourth electrical poles 24. The third and fourth poles 24 are also spaced apart and separated from each other so that there is no direct electrical contact between the third and fourth poles 24. Preferably, the first, second, third and fourth poles 22, 24 are attached to the insulation layer 18 by adhering the poles 22, 24 to the insulation layer 18 with adhesives or other bonding techniques.

As those of ordinary skill in the art understand, when an electrical charge is applied by a bipolar generator between the first and second poles 22, the space 23 separating the first and second poles 22 causes adjacent tissue to be ablated. Likewise, an electrical charge can be applied to the third and fourth poles 24 by a bipolar generator so that the space 25 between the third and fourth poles 24 causes adjacent tissue to also be ablated. Because the electrical charge that is applied to the first and second poles 22 may be different from the electrical charge that is applied to the third and fourth poles 24, improved control over ablation may be possible. For example, it may be desirable to apply an electrical charge that is more intense to the third and fourth poles 24 then the electrical charge that is applied to the first and second poles 22. By adjusting electrical charges applied to the first and second poles 22 and the third and fourth poles 24, it may be possible to provide different ablation characteristics to the tissue adjacent the outside of the loop 12 and the tissue adjacent the inside of the loop 12. For example, the electrical charge applied to the first and second poles 22 may ablate the outside tissues sufficiently to cauterize the tissue while minimizing damage to the outside tissue. On the other hand, the electrical charge applied to the third and fourth poles 24 may ablate the inside tissues sufficiently to kill a deeper region of the inside tissue. Thus, in the case of a tumor, where the loop 12 is rotated around the tumor, the healthy tissue around the outside of the first and second poles 22 may be cauterized to provide a sealed boundary around the tumor. The tumor tissue inside the third and fourth poles 24 may also be killed to a greater extent than the healthy tissue on the outside of the loop 12. As a result, it may be easier to control ablation of a tumor to maximize the tumor tissue that is killed while minimizing the healthy tissue that is damaged. In addition, it may be possible to form a cauterized seal around the tumor to isolate any surviving tumor tissue from the rest of the body. This may cause the remaining tumor tissue to die naturally since it is cut off from the blood supply of the body.

In yet another possible use of the medical instrument, the loop 12 may be rotated around a tumor multiple times and the electrical charge applied to the inner and outer electrodes 14, 16 may be changed between rotations. For example, during the first rotation, electrical charges may be applied to both the inner and outer electrodes 14, 16 to isolate the tumor and cauterize the healthy tissue outside the loop 12. In subsequent rotations, an electrical charge may be applied only to the inner electrode 14 or a higher charge may be applied to the inner electrode 14 to more deeply kill the tumor.

Figure 4:
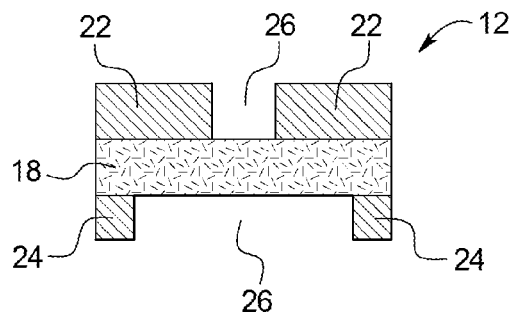
FIG. 4 is a cross-section view of one embodiment of a loop with inner and outer electrodes.
Figure 5:
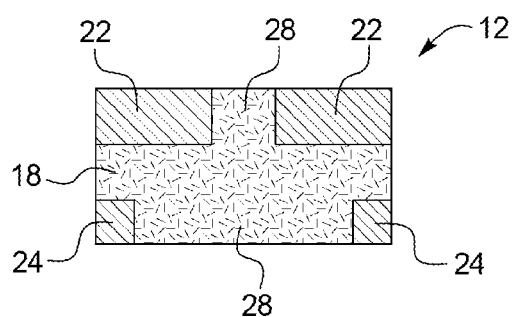
FIG. 5 is a cross-section view of another embodiment of a loop with inner and outer electrodes.

In addition to adjusting electrical charges to the inner and outer electrodes 14, 16, the space 23 between the first and second poles 22 can be different than the space 25 between the third and fourth poles 24. The size and shape of the first and second poles 22 may also be different than the size and shape of the third and fourth poles 24. For example, as shown in FIGS. 2 and 3, the space 23 between the first and second poles 22 may be shorter than the space 25 between the third and fourth poles 24. The width of the first and second poles 22 may also be wider than the width of the third and fourth poles 24. For example, the first and second poles 22 may be thin, flat ribbons with the wider surfaces facing outward and the corresponding rear surfaces of the poles 22 glued to the insulation layer 18. The third and fourth poles 24 may be wires that are partially embedded in the insulation layer 18 or may be other narrow shapes and may be attached to the insulation layer 18 in other ways. As a result of the shape and spacing of the first, second, third and fourth poles 22, 24, the electrical charge of the inner electrode 14 may be more intense than the electrical charge of the outer electrodes 16. As described above, this may be useful to maximize ablation of a tumor inside the loop 12 and minimize ablation outside the loop 12. By providing first and second poles 22 that are structurally different from the third and fourth poles 24, it may also be easier for a physician to adjust the electrical charges at the inner and outer electrodes 14, 16 to achieve the desired ablation characteristics. As shown in FIG. 4, the first and second poles 22 of the outer electrodes 16 are on the opposite side of the insulation layer 18 from the third and fourth poles 24 of the inner electrode 14. Thus, as described above, the inner and outer electrodes 14, 16 are insulated from each other. As further shown in FIG. 4, the spaces 23, 25 between the first and second poles 22 and the third and fourth poles 24 may be open spaces 26 so that the first, second, third and fourth poles 22, 24 extend out from the insulation layer 18. Alternatively, as shown FIG. 5, portions 28 of the insulation layer 18, or another type of insulation, may fill the space 23 between the first and second poles 22 and the space 25 between the third and fourth poles 24 so that the portions 28 extend to at least the outer surface of the outer electrode 16 and inner surface of the inner electrode 14. One advantage of this design may be that tissue is prevented from ingressing into the spaces 23, 25 between the poles 22, 24.

Figure 6:
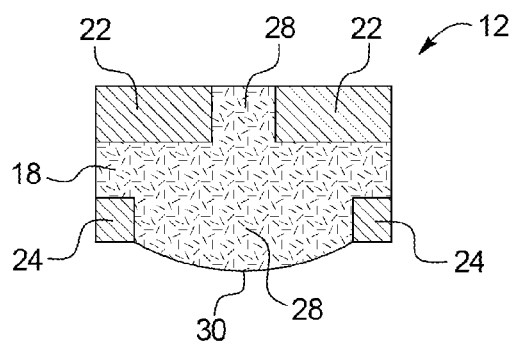
FIG. 6 is a cross-section view of another embodiment of a loop with inner and outer electrodes.
Figure 7:
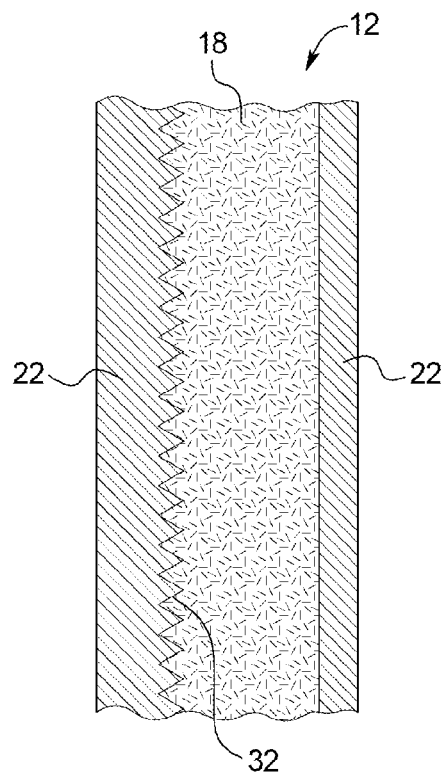
FIG. 7 is a top view of the inner electrode of another embodiment of a loop.

It may also be desirable to add structures that further enhance the ablation characteristics of the medical instrument 10. For example, as shown in FIG. 6, a raised portion 30 of insulation may be provided between the third and fourth poles 24 of the inner electrode 14. This may be desirable to enhance the effects of the electrical charge at the inner electrode 14 to maximize tissue ablation inside the loop 12. As shown in FIG. 7, it may also be desirable to provide the third or fourth or both poles 24 with teeth 32 facing the other pole 24. This may further enhance the electrical charge at the inner electrode 14.

Figure 8:
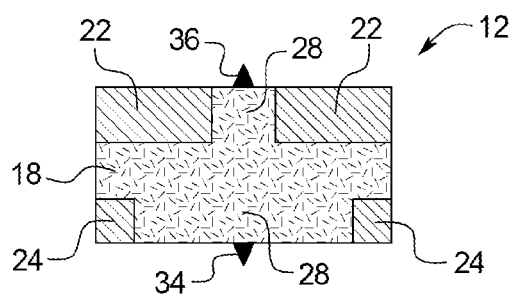
FIG. 8 is a cross-section view of another embodiment of a loop with inner and outer electrodes.

As shown in FIG. 8, it may also be desirable to provide the medical instrument 10 with cutting blades 34, 36 on the outside, inside or both sides of the loop 12. The cutting blades 34, 36 may be attached to the insulation layer 18 between the first and second poles 22 and the third and fourth poles 24. Thus, an outer blade 36 may be provided between the first and second poles 22 that extends outward from the outer surfaces of the first and second poles 22. Likewise, an inner blade 34 may be provided between the third and fourth poles 24 and may extend inward from the inner surfaces of the third and fourth poles 24. The sharp tip 20 described above may be attached to the insulation layer 18 between the first and second poles 22 in a similar manner. Preferably, the inner and outer cutting blades 34, 36 and the sharp tip 20 are made from a non-conductive material to avoid interference with the electrical charge applied to the first, second, third and fourth poles 22, 24. Alternatively, the cutting blades 34, 36 and/or the sharp tip 20 may also be made from a non-ferrous material or may be made from a ferrous metal. Preferably, the cutting blades 34, 36 extend around the majority of the loop 12 and may extend substantially around the entirety of the loop 12. As described below, the sharp tip 20 and cutting blades 34, 36 may be useful in delivering the loop 12 to the treatment site and retracting the loop 12 after the ablation procedure.

Figure 9:
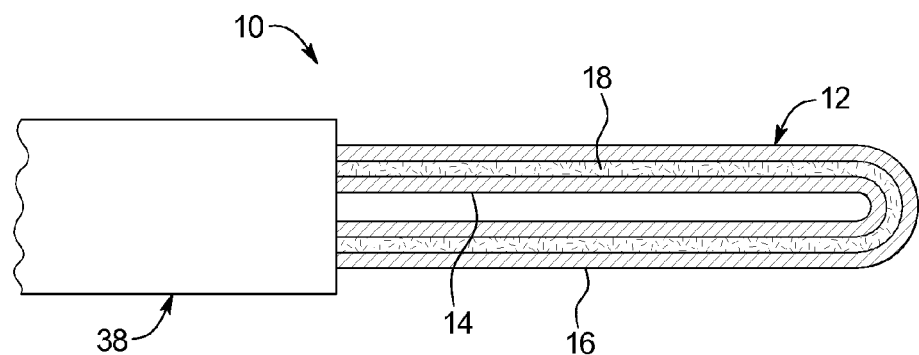
FIG. 9 is a side view of a loop in a collapsed configuration.

As shown in FIGS. 1 and 9, in one embodiment of the medical instrument 10, one or more of the poles 22, 24 may be made from self-expanding nitinol. In this embodiment, the unstressed state of the nitinol poles 22, 24 may be a loop 12, such as the circular loop 12 shown in FIG. 1. Thus, as shown in FIG. 9, the electrodes 14, 16 and insulation layer 18 may be compressed into a collapsed configuration where the opposing sides of a circular loop 12 are generally adjacent each other. In the collapsed configuration, the loop 12 forms a low profile that can slide through a delivery catheter 38. Typically, the delivery catheter 38 restrains the self-expanding nitinol poles 22, 24 in the collapsed configuration by preventing the poles 22, 24 from expanding when the loop 12 is inside of the catheter 38. However, when the loop 12 is released from the catheter 38, either by withdrawing the catheter 38 or by pushing the loop 12 out of the catheter 38, the poles 22, 24 elastically expand to the unstressed shape of the nitinol poles 22, 24.

Figure 10:
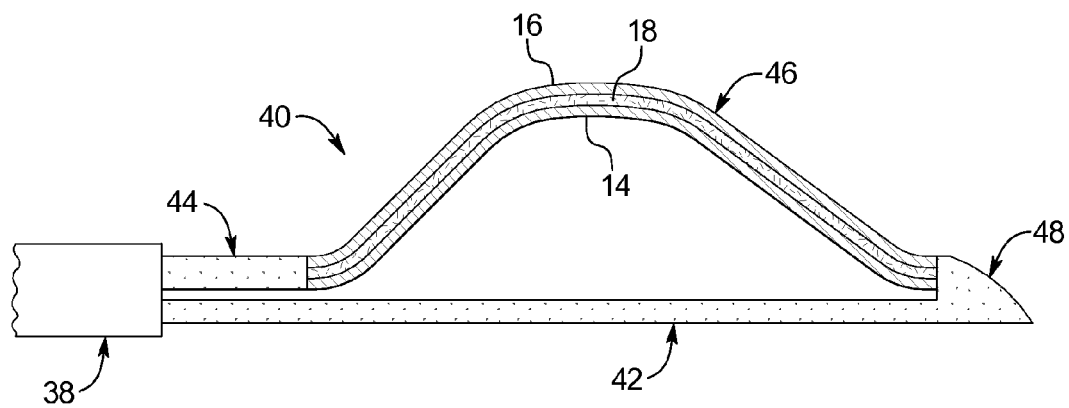
FIG. 10 is a side view of another loop in an expanded configuration.

As shown in FIG. 10, an alternative embodiment of the medical instrument 40 can be expanded and retracted by moving two longitudinal members 42, 44 relative to each other. For example, a first longitudinal member 42 may be attached to the distal end of the loop 46 and a second longitudinal member 44 may be attached to the proximal end of the loop 46. A sharp distal tip 48 may also be provided at the distal end of the loop 46 and the first longitudinal member 42. In this embodiment, the loop 46 may be made from materials that are less elastic than self-expanding nitinol. For example, metals with conventional elasticity may be preferable. Accordingly, the loop 46 may be collapsed to slide the loop 46 through a delivery catheter 38 by moving the ends of the first and second longitudinal members 42, 44 away from each other. This causes the loop 46 to stretch and flatten alongside the first longitudinal member 42. To expand the loop 46, the ends of the first and second longitudinal members 42, 44 may be moved toward each other. This causes the loop 46 to compress and forces the center of the loop 46 away from the first longitudinal member 42.

As described above, the medical instrument 10, 40 may be particularly useful for treating tumors by ablating a circumferential region around the tumor. This is accomplished by rotating a loop 12, 46 with bipolar electrodes 14, 16 around the tumor. This may have the results of killing substantially all of the tumor tissue or sufficiently isolating the tumor from the surrounding healthy tissue and blood supply so that the tumor dies from a lack of nutrients. Because the medical instrument 10, 40 provides inner and outer electrodes 14, 16 that can be operated independently of each other, damage to the surrounding healthy tissue can be minimized and damage to the tumor tissue can be maximized. Thus, the healthy tissue can be ablated sufficiently to cauterize a zone around the tumor tissue without causing extensive damage to the healthy tissue. A more intense ablation may then be applied to the tumor tissue. The inner and outer electrodes 14, 16 may be used simultaneously with different ablation intensity supplied to the electrodes 14, 16, or the inner and outer electrodes 14, 16 may be used in alternating or overlapping sequences. In addition, the size, shape, spacing, materials and separating structures may be different from each other for the inner and outer electrodes 14, 16 so that the ablation characteristics of the inner and outer electrodes 14, 16 are different from each other. Cutting members 20, 34, 36, 48 may also be provided to aid in deploying the loop 12, 46 and retracting the loop 12, 46. For example, a sharp distal tip 20, 48 may be provided to allow the loop 12, 46 to be pushed through tissue by piercing the tissue. The cutting blade 36 may also be provided around the outside of the loop 12, 46 to allow the loop 12, 46 to be expanded by slicing through tissue as the loop 12, 46 expands. Another cutting blade 34 may also be provided around the inside of the loop 12, 46 to allow the loop 12, 46 to be collapsed again after the ablation is completed by slicing through tissue as the loop 12, 46 is retracted. Alternatively, if cutting members are not used, the electrodes 14, 16 may be used to ablate through tissue during deployment and retraction to permit the loop 12, 46 to expand and collapse.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A medical instrument for ablating tissue, comprising:
   first and second electrical poles extending around a loop configuration, said first and second poles being spaced apart from each other at least a first distance around said loop configuration, said first and second poles being capable of providing a first electrical charge across said first distance;
   third and fourth electrical poles extending around said loop configuration, said third and fourth poles being spaced apart from each other at least a second distance around said loop configuration, said third and fourth poles being capable of providing a second electrical charge across said second distance;
   an insulation layer separating said first and second poles from said third and fourth poles, said first and second poles facing toward an exterior of said loop configuration and said third and fourth poles facing toward an inner region of said loop configuration;
   wherein said loop configuration is rotatable around a tissue portion to ablate tissue circumferentially around said tissue portion to thereby isolate said tissue portion from adjacent tissue, said first and second electrical charges being independent of each other.

2. The medical instrument according to claim 1, wherein said first distance is narrower than said second distance.

3. The medical instrument according to claim 1, wherein at least one of said third and fourth poles comprises teeth facing toward the other of said first and second poles.

4. The medical instrument according to claim 1, wherein said first and second poles are flat ribbons comprising a thickness and a width wider than said thickness, said width facing toward said exterior and an inner surface of said width being adhered to said insulation layer.

5. The medical instrument according to claim 1, further comprising a non-conductive sharp tip disposed at a distal end of said loop configuration, said sharp tip being attached to said insulation layer and extending outward from between said first and second poles.

6. The medical instrument according to claim 1, wherein an open space extending across said first distance is disposed between said first and second poles.

7. The medical instrument according to claim 1, further comprising a non-conductive cutting blade disposed around a majority of said loop configuration, said cutting blade being attached to said insulation layer and extending outward from between said first and second poles.

8. The medical instrument according to claim 1, further comprising a raised insulation portion disposed around said loop configuration between said third and fourth poles, said raised insulation portion being attached to said insulation layer and extending between and inward beyond inner facing surfaces of said third and fourth poles.

9. The medical instrument according to claim 1, further comprising a non-conductive cutting blade disposed around a majority of said loop configuration, said cutting blade being attached to said insulation layer and extending inward from between said third and fourth poles.

10. The medical instrument according to claim 1, further comprising an insulation portion disposed around said loop configuration between said third and fourth poles, said insulation portion being attached to said insulation layer and extending between and inward at least to inner facing surfaces of said third and fourth poles.

11. The medical instrument according to claim 1, further comprising an insulation portion disposed around said loop configuration between said first and second poles, said insulation portion being attached to said insulation layer and extending between and outward at least to outer facing surfaces of said first and second poles.

12. The medical instrument according to claim 1, wherein said first and second poles and said third and fourth poles are made from self-expanding nitinol with an unstressed state in said loop configuration, said first and second poles and said third and fourth poles being compressible into a collapsed configuration adapted to slide within a catheter.

13. The medical instrument according to claim 1, wherein a distal end of said loop configuration is attached to a first longitudinal member and a proximal end of said loop configuration is attached to a second longitudinal member, said first and second longitudinal members being axially moveable relative to each other to stretch and compress said first and second poles and said third and fourth poles between said loop configuration and a collapsed configuration.

14. The medical instrument according to claim 1, wherein said first distance is narrower than said second distance, said first and second poles are flat ribbons comprising a thickness and a width wider than said thickness, said width facing toward said exterior and an inner surface of said width being adhered to said insulation layer, further comprising a first insulation portion disposed around said loop configuration between said first and second poles, said first insulation portion being attached to said insulation layer and extending between and outward at least to outer facing surfaces of said first and second poles, and further comprising a second insulation portion disposed around said loop configuration between said third and fourth poles, said second insulation portion being attached to said insulation layer and extending between and inward at least to inner facing surfaces of said third and fourth poles.

15. The medical instrument according to claim 14, further comprising a non-conductive sharp tip disposed at a distal end of said loop configuration, said sharp tip being attached to said insulation layer and extending outward from between said first and second poles.

16. The medical instrument according to claim 15, further comprising a non-conductive cutting blade disposed around a majority of said loop configuration, said cutting blade being attached to said insulation layer and extending outward from between said first and second poles, and further comprising a raised insulation portion disposed around said loop configuration between said third and fourth poles, said raised insulation portion being attached to said insulation layer and extending between and inward beyond inner facing surfaces of said third and fourth poles.

17. The medical instrument according to claim 16, wherein said first and second poles and said third and fourth poles are made from self-expanding nitinol with an unstressed state in said loop configuration, said first and second poles and said third and fourth poles being compressible into a collapsed configuration adapted to slide within a catheter.

18. The medical instrument according to claim 1, wherein said first and second poles are flat ribbons comprising a thickness and a width wider than said thickness, said width facing toward said exterior and an inner surface of said width being adhered to said insulation layer, further comprising a non-conductive sharp tip disposed at a distal end of said loop configuration, said sharp tip being attached to said insulation layer and extending outward from between said first and second poles, and further comprising a raised insulation portion disposed around said loop configuration between said third and fourth poles, said raised insulation portion being attached to said insulation layer and extending between and inward beyond inner facing surfaces of said third and fourth poles.

19. The medical instrument according to claim 18, further comprising a non-conductive cutting blade disposed around a majority of said loop configuration, said cutting blade being attached to said insulation layer and extending outward from between said first and second poles, and further comprising an insulation portion disposed around said loop configuration between said first and second poles, said insulation portion being attached to said insulation layer and extending between and outward at least to outer facing surfaces of said first and second poles.

20. The medical instrument according to claim 19, wherein said first distance is narrower than said second distance, and said first and second poles and said third and fourth poles are made from self-expanding nitinol with an unstressed state in said loop configuration, said first and second poles and said third and fourth poles being compressible into a collapsed configuration adapted to slide within a catheter.

* * * * *